(12) United States Patent
Marvin et al.

(10) Patent No.: US 9,120,720 B2
(45) Date of Patent: Sep. 1, 2015

(54) PROCESS FOR MAKING ETHANOLAMINES

(71) Applicant: Scientific Design Company, Inc., Little Ferry, NJ (US)

(72) Inventors: Katelyn Marvin, Maplewood, NJ (US); Barry Jay Billig, Irvington, NY (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/578,795

(22) Filed: Dec. 22, 2014

(65) Prior Publication Data

US 2015/0183720 A1 Jul. 2, 2015

Related U.S. Application Data

(60) Provisional application No. 61/921,820, filed on Dec. 30, 2013.

(51) Int. Cl.
*C07C 213/10* (2006.01)
*C07C 213/04* (2006.01)

(52) U.S. Cl.
CPC ............. *C07C 213/10* (2013.01); *C07C 213/04* (2013.01)

(58) Field of Classification Search
CPC .................................................. C07C 213/04
See application file for complete search history.

(56) References Cited

U.S. PATENT DOCUMENTS

| | | | |
|---|---|---|---|
| 2,196,554 A | 4/1940 | Guinot | |
| 3,563,914 A | 2/1971 | Wattimena | |
| 3,702,259 A | 11/1972 | Nielsen | |
| 3,962,285 A | 6/1976 | Cusumano | |
| 4,119,670 A | 10/1978 | Tsuchiya | |
| 4,169,856 A | 10/1979 | Cocuzza et al. | |
| 4,355,181 A * | 10/1982 | Willis et al. | 564/477 |
| 4,761,394 A | 8/1988 | Lauritzen | |
| 4,766,105 A | 8/1988 | Lauritzen | |
| 4,845,296 A | 7/1989 | Ahmed et al. | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,187,140 A | 2/1993 | Thorsteinson et al. | |
| 5,407,888 A | 4/1995 | Herzog et al. | |
| 2007/0037991 A1 | 2/2007 | Rizkalla | |
| 2010/0087684 A1 | 4/2010 | Do et al. | |

FOREIGN PATENT DOCUMENTS

| | | |
|---|---|---|
| EP | 2 177 501 A1 | 4/2010 |
| GB | 760215 | 10/1956 |
| GB | 1529193 | 10/1978 |

OTHER PUBLICATIONS

International Search Report and Written Opinion dated Apr. 1, 2015 received in corresponding foreign International Application No. PCT/US2014/071822.

* cited by examiner

*Primary Examiner* — Brian J Davis

(74) *Attorney, Agent, or Firm* — Scully, Scott, Murphy & Presser, P.C.

(57) ABSTRACT

A process for the preparation of ethanolamines comprising reacting a water-ammonia solution comprising ammonia and water with ethylene oxide.

11 Claims, 1 Drawing Sheet

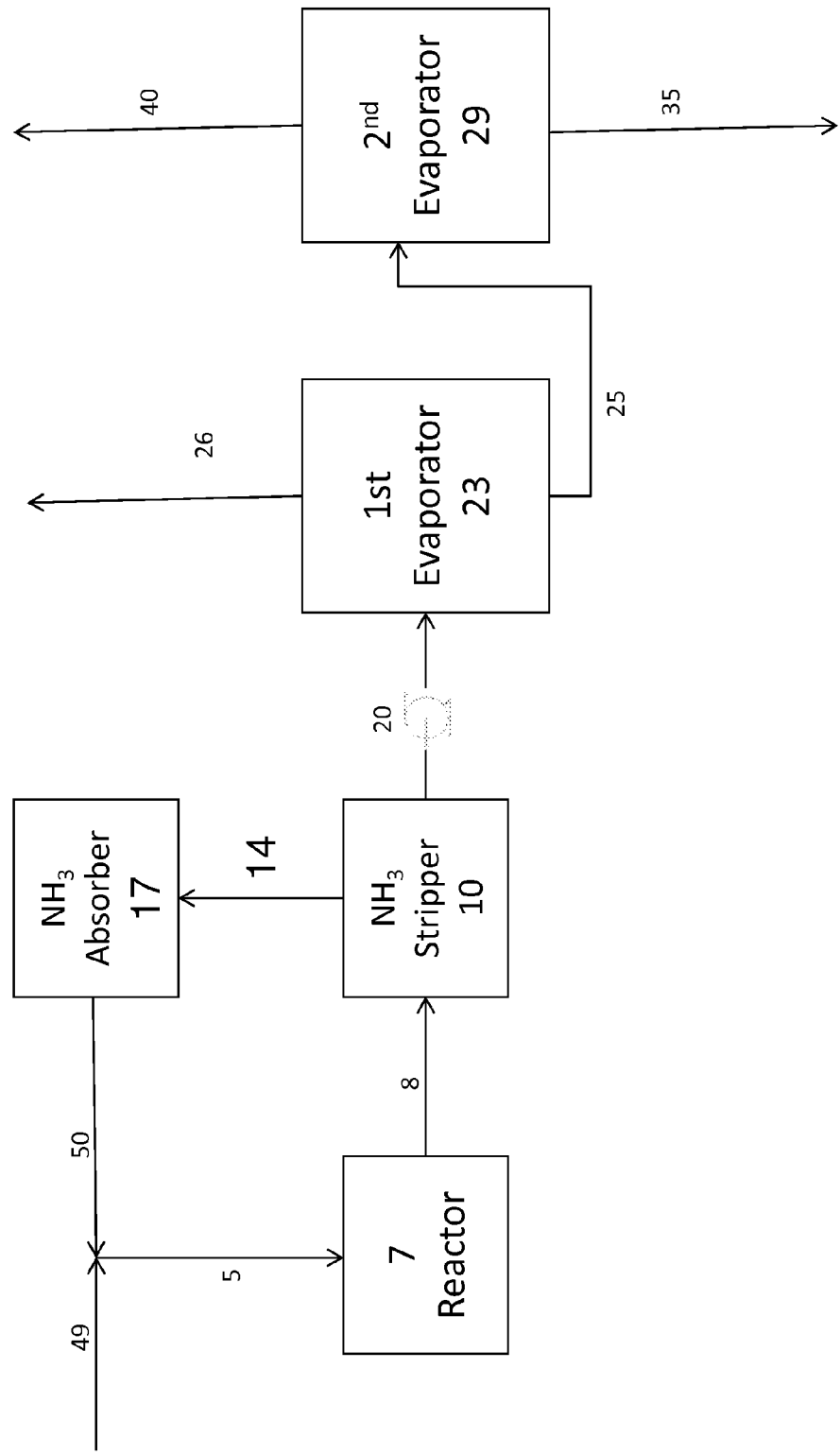

PROCESS FOR MAKING ETHANOLAMINES

CROSS REFERENCE TO RELATED APPLICATION

The present invention claims the benefit of U.S. Provisional Patent Application No. 61/921,820 filed Dec. 30, 2013, the entire content and disclosure of which is incorporated herein by reference.

FIELD OF THE INVENTION

The present invention relates to a method for the production of ethanolamines by reacting ammonia and ethylene oxide.

BACKGROUND OF THE INVENTION

Ethanolamines were first synthesized in a laboratory setting in 1860 when the pioneering Alsatian chemist Charles-Adolphe Wurtz heated ethylene chlorohydrin with aqueous ammonia in a closed tube. While never commercially interesting during the nineteenth century, ethanolamines were nonetheless enough of a technical curiosity that they attracted considerable technical interest. For example, the great German chemist Ludwig Knorr significantly improved upon Wurtz's work when in 1897 he successfully separated ethanolamines into their mono-, di- and triethanolamine component parts, as well as made other contributions to their synthesis.

Despite process improvements and continued laboratory interest, ethanolamines only attracted substantial commercial development after 1945. At this time, the significant increase in the industrial production of ethylene oxide was also leading to considerable interest in ethylene oxide derivatives. Ironically, this commercial movement from ethylene oxide to ethanolamines recapitulated the history of the synthesis of the chemicals as Wurtz's synthesis of ethanolamines in 1860 was largely the result of his trying to figure out what he could make with a new chemical he had discovered just the year before—ethylene oxide.

In the post-war years, significant process improvements were subsequently made as a result of the burgeoning interest in ethanolamines, which had proven to be extremely versatile intermediates in a wide variety of chemical products such as emulsifiers, surfactants, and agrichemicals, as well as many others. Examples of such improvement can be seen in, for example, U.S. Pat. No. 2,196,554 to Guinot which discloses an aqueous process with an improved heat integration and efficiency scheme for the concentration of ethanolamines in the process backend. Another example is GB Patent No. 760,215 to Lowe et al., which discloses that by controlling the molar ratios at which ammonia and ethylene oxide are mixed, then a higher content of di- or tri-ethanolamine may be obtained. Alternatively, GB Patent No. 1 529 193 to Gleich discloses that a higher di- or tri-ethanolamine content may be obtained by recycling di- or tri-ethanolamine to the reactor.

Given that the conversion of reactants to products is nearly complete in an ethanolamines process and the fact that the process has developed into a mature technology by process improvements such as those mentioned above, wringing out additional improvements or competitive technical advantages in ethanolamines technology has proved difficult.

Accordingly, there is a continuing need in the art for an ethanolamine manufacturing process with the improved process economics and efficiency of operating at high ammonia to water ratios and that also produces quality, on-spec product.

BRIEF SUMMARY OF THE INVENTION

The present invention relates to a process for the preparation of ethanolamines comprising the steps of: (a) mixing a water-ammonia solution comprising from about 20% to about 60% ammonia and about 40% to about 80% water with ethylene oxide to form a reactor inlet composition; (b) charging the reactor inlet composition to one or more amine reactors; (c) reacting the ammonia with the ethylene oxide in the one or more amine reactors to form an effluent reaction mixture comprising unreacted ammonia, water and ethanolamines; (d) separating, in a stripping column, the effluent reaction mixture into a rich ammonia-water mixture vapor overhead and a product solution bottoms liquid; (e) mixing the rich ammonia-water mixture with liquid ammonia in an ammonia absorber to prepare the water-ammonia solution; and (f) separating, in a first evaporator, the product solution into a concentrated product solution bottoms liquid and a steam overhead.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 is a schematic flow sheet for a process for preparing ethanolamines according to the present invention.

DETAILED DESCRIPTION OF THE INVENTION

All parts, percentages and ratios used herein are expressed by volume unless otherwise specified. All documents cited herein are incorporated by reference.

By "water" it is meant any kind of water suitable for use in chemical and petrochemical processing, including deionized, demineralized, industrial, potable and distilled water.

The process of the present invention will now be described in detail with specific reference to FIG. 1. A reactor inlet composition is prepared by combining a source of ethylene oxide 49 with a water-ammonia solution. Preferably, this water-ammonia solution is a water-ammonia solution that is prepared in an ammonia absorber 17 (described below) and supplied through conduit 50. The water-ammonia solution comprises from about 20% to about 60% ammonia and about 40% to about 80% water, preferably the water-ammonia solution comprises from about 45% to about 55% ammonia and about 45% to about 55% water. The reactor inlet composition contains ammonia and ethylene oxide at a molar ratio of about 4:1 to about 12:1 ammonia:ethylene oxide, preferably the ratio of ammonia:ethylene oxide is about 10:1 to about 12:1. The desired mix of final product between monoethanolamine, diethanolamine, and triethanolamine may be obtained by controlling the molar ratios at which ammonia and ethylene oxide are mixed, then a higher content of di- or tri-ethanolamine may be obtained.

The reactor inlet composition is fed through conduit 5 to the one or more amine reactors (a single reactor 7 is shown in FIG. 1). Either adiabatic, isothermal or a combination of both reactors may be used in the process. Preferably a series of tubular reactors are used. The one or more reactors are operated at a temperature and pressure to prevent vaporization of any of the components in the reactor inlet composition and ensure single-phase liquid operation. Accordingly, the temperature in the reactors should be maintained between 30° C. and 75° C. and the pressure between 1.0 MPa and 2.0 MPa. The ethylene oxide mixes with excess ammonia in the amine reactor so that the conversion of the ethylene oxide is nearly complete. The effluent reaction mixture from the one or more reactors is composed of ethanolamines (mono-, di-, and tri-) as well as unreacted ammonia and water. This effluent reaction mixture flows by pressure differential through conduit 8 to arrive at the ammonia stripping column 10 (hence the pressure in the first stripping column must be maintained less than that in the one or more reactors—preferably the pressure in the first stripping column is from about 0.45 MPa to about 0.65 MPa). Before arriving at the ammonia stripping column 10, the effluent reaction mixture is preferably heated to a temperature of between 80° C. and 120° C. (In FIG. 1, this heating step is not shown).

In the (ammonia) stripping column 10 substantially all of the unreacted ammonia is separated from the effluent reaction mixture. As the effluent reaction mixture moves downward in the column, separation by steam-stripping of the effluent reaction mixture takes place with the upwardly-moving steam (provided by a steam source, such as an adjacent reboiler, not shown) contacting the effluent reaction mixture and separating the more volatile components from the mixture, especially the unreacted ammonia, i.e., the ammonia that did not react with ethylene oxide in the reactor 7. A key advantage of this invention is that substantially all of the unreacted ammonia in the effluent reaction mixture is separated from the effluent reaction mixture in a single step in the stripping column 10—in order to do this, the stripping column must be operated at a bottoms temperature of between 80° C. and 130° C. This unreacted ammonia is separated from the effluent reactor mixture and passes along with water as vapor to the overhead of the stripping column. Thus, an ammonia-water mixture (rich in ammonia) is formed as vapor in the stripper overhead comprising the unreacted ammonia, water vapor and optionally other components in the vapor phase. Thus substantially all of the unreacted ammonia is contained by the ammonia-water mixture and this ammonia-water mixture comprises substantially all of the unreacted ammonia. By "substantially all of the unreacted ammonia" it is meant greater than 90% of the unreacted ammonia.

The ammonia-water mixture in the stripping column overhead flows through conduit 14 by pressure differential to the ammonia absorber 17 (and so by definition the ammonia absorber 17 is operated at a pressure that is less than the pressure of the first ammonia stripper 10). The stripping column is operated at an overhead pressure of about 0.15 MPa to about 0.65 MPa. The ammonia absorber is operated at overhead pressure of about 0.1 MPa to about 0.6 MPa. As mentioned above, the water-ammonia solution that is supplied to reactor is prepared in the ammonia absorber 17. Make-up liquid ammonia may be added to the ammonia absorber 17 and mixed with the ammonia-water mixture in order to replace the ammonia used in the reaction and maintain the ammonia concentration in the water-ammonia solution at the levels disclosed above. This water-ammonia solution is then supplied through conduit 50 to be combined with a source of ethylene oxide to form the reactor inlet composition.

A product solution is formed in the bottom of the stripping column 10 comprising water and ethanolamines. Substantially all of the ethanolamines product is contained in this product solution. This product solution may also contain small quantities of other less volatile components of the effluent reaction mixture and may also include trace quantities of ammonia—though as discussed above the present process is very efficient at separating ammonia into the overhead vapor phase. This product solution preferably comprises about 70% to 85% water and about 15% to about 30% ethanolamines. This product solution is taken from the stripping column 10 as a liquid bottoms stream and pumped through conduit 20 to the first evaporator 23. The action of the first evaporator 23 taken together with the second evaporator 29 is to significantly concentrate the product solution. By "substantially all of the ethanolamines product" it is meant greater than 90% of the ethanolamines product is contained in the product solution.

In the first evaporator 23, as the product solution moves downward in the evaporator column, separation by steam-stripping of the product solution takes places with upwardly-moving steam contacting the product solution and separating the water and other more volatile components from the product solution to produce a concentrated product solution, which as a result of the steam stripping has a higher concentration of ethanolamines and other less volatile components. Steam may be provided by for example, a reboiler (not shown) situated adjacent to the first evaporator 23 or the steam may be provided by some other suitable source. The overhead pressure in the first evaporator column is maintained at from about 0.8 MPa to about 1.2 MPa, while the temperature of the concentrated product solution in bottom of the first evaporator column is from about 170° C. to about 190° C.

The concentrated product solution flows from the first evaporator by pressure differential through conduit 25 to the second evaporator 29. The overhead vapor (steam) from the first evaporator 23 is supplied through conduit 26 to provide a heat and vapor source to the second evaporator 29 or to an adjacent reboiler (not shown). The second evaporator 29 functions identical to the first evaporator 23, wherein a concentrated ethanolamines solution is prepared by the steam stripping of the more volatile components, especially water, from the concentrated production solution. The result is a concentrated ethanolamines solution that is preferably from about 35 wt % to about 55 wt % ethanolamines, and the balance water. As mentioned above, the effect of the first evaporator and second evaporator is to significantly increase the ethanolamines concentration of the product solution that was produced in the ammonia absorber to result in a concentrated ethanolamines solution with a much higher concentration of ethanolamines. The overhead pressure in the second evaporator column is maintained at from about 0.25 MPa to about 0.5 MPa, while the temperature of the concentrated product solution in bottom of the second evaporator column is from about 140° C. to about 160° C.

The concentrated ethanolamines solution is sent from the bottoms stream through conduit 35 to a drying column (not shown) to reduce the water content even further, then to refining and separation steps (not shown). The overhead vapor (steam) exits from the second evaporator 39 through conduit 40 and it may be integrated into the process in a variety of different ways, but most preferably is used as a vapor and heat source for the ammonia stripper or ammonia stripper reboiler (not shown).

The stripping column 10, the absorber 17 the first evaporator 23 and the second evaporator 29 are constructed so as to facilitate intimate vapor-liquid contact and any suitable arrangement or configuration that accomplishes this is acceptable. The columns' internals may selected from either multiple-tray configurations or random or structured packing.

Ethylene Oxide Production

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 43% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process. Both have adverse effects on the catalyst, so the concentrations of these components are usually kept at a minimum.

Also present in the reaction, as previously mentioned, are one or more chloride moderators. Non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

A usual method for the ethylene epoxidation process comprises the vapor-phase oxidation of ethylene with molecular oxygen, in the presence of an epoxidation catalyst (to be defined in greater detail herein below), in a fixed-bed tubular reactor. Conventional, commercial fixed-bed ethylene-oxide reactors are typically in the form of a plurality of parallel elongated tubes (in a suitable shell) approximately 20 to 70 mm O.D. and 15 to 65 mm I.D. and 5-16 meters long filled with catalyst. Such reactors include a reactor outlet which allows the olefin oxide, un-used reactants, and byproducts to exit the reactor chamber.

The ethylene oxide that is reacted with ammonia in the present invention may be supplied from OSBL or may be supplied by an ethylene oxide process that is integrated with the ethanolamines process in the same chemical complex.

Epoxidation Catalyst

The epoxidation catalyst that can be used in the present invention includes a silver-based epoxidation catalyst that has a selectivity of greater than 83 mole %. The silver-based epoxidation catalyst that can be used in the present invention includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. In one embodiment of the present application, the epoxidation catalyst that can be used is a silver-based, rhenium-containing epoxidation catalyst which may also include one or more additional promoters. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. Equivalent diameter is the diameter of a sphere having the same external surface (i.e., neglecting surface within the pores of the particle) to volume ratio as the support particles being employed.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

In some embodiments of the present invention, a promoting amount of a rhenium component, which may be a rhenium-containing compound or a rhenium-containing complex is also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and, if present, rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), optional rhenium component, and optional additional promoter(s) will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include operability (resistance to runaway), selectivity, activity, conversion, stability and yield, among other catalytic properties. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various promoters can be employed.

After impregnation of the support with the silver-containing compound, i.e., a silver precursor, optional promoters such as, for example, rhenium and/or alkali metals, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial ethylene oxide reactor units: a gas hourly space velocity (GHSV) of 1500-10,000 $h^{-1}$, a reactor inlet pressure of 1 Mpa to 3 MPa, a coolant temperature of 180-315° C., an oxygen conversion level of 10-60%, and an EO production rate (work rate) of 100-350 kg EO/$m^3$ catalyst/hr and a change in ethylene oxide concentration, $\Delta$EO, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

We claim:

1. A process for the preparation of ethanolamines comprising the steps of:
   (a) mixing a water-ammonia solution comprising from about 20% to about 60% ammonia and about 40% to about 80% water with ethylene oxide to form a reactor inlet composition;
   (b) charging the reactor inlet composition to one or more amine reactors;
   (c) reacting the ammonia with the ethylene oxide in the one or more amine reactors to form an effluent reaction mixture comprising unreacted ammonia, water and ethanolamines;
   (d) separating, in a stripping column, the effluent reaction mixture into a rich ammonia-water mixture vapor overhead and a product solution bottoms liquid;
   (e) mixing the rich ammonia-water mixture vapor overhead with liquid ammonia in an ammonia absorber to prepare the water-ammonia solution; and (f) separating, in a first evaporator, the product solution into a concentrated product solution bottoms liquid and a steam overhead.

2. The process according to claim 1, wherein the ammonia-water mixture vapor overhead comprises substantially all of the unreacted ammonia.

3. The process according to claim 1, where the ammonia and ethylene oxide are present in a molar ratio of ammonia:ethylene oxide of, about 4:1 to about 12:1.

4. The process according to claim 1, further comprising the step of passing the steam overhead from the first evaporator to provide a second evaporator with a source of vapor and heat.

5. The process according to claim 1, wherein the stripping column is operated at a bottoms temperature of from about 80° C. to about 130° C.

6. The process according to claim 1, further comprising the step of passing the rich ammonia-water mixture vapor overhead from the stripping column by pressure differential to the ammonia absorber.

7. The process according to claim 6, wherein the pressure in the stripping column overhead is between about 0.15 MPa to about 0.65 MPa.

8. The process according to claim 1, wherein the ethylene oxide is manufactured by contacting an oxygen-containing gas with ethylene in the presence of an epoxidation catalyst.

9. The process according to claim 8, wherein the epoxidation catalyst is a silver-based epoxidation catalyst that includes a promoting amount of rhenium.

10. The process according to claim 1, wherein the product solution comprises substantially all of the ethanolamines product.

11. The process according to claim 9, wherein the product solution comprises from about 15% to about 30% ethanolamines and about 70% to about 85% water.

* * * * *